United States Patent [19]
Lagrange

[11] Patent Number: 6,123,952
[45] Date of Patent: Sep. 26, 2000

[54] USE OF PHOTOCHROMIC COLORING AGENT IN A COSMETIC COMPOSITION, AND COSMETIC COMPOSITION COMPRISING IT

[75] Inventor: Alain Lagrange, Coupvray, France

[73] Assignee: L'Oreal, Paris, France

[21] Appl. No.: 09/209,002

[22] Filed: Dec. 11, 1998

[30] Foreign Application Priority Data

Dec. 12, 1997 [FR] France ................... 97 15769

[51] Int. Cl.⁷ ............... A61K 7/00; A61K 7/42; A61K 7/035; A61K 7/06
[52] U.S. Cl. ............. 424/401; 424/59; 424/60; 424/69; 424/70.1; 424/400
[58] Field of Search .................. 424/59, 60, 69, 424/400, 70.1, 401

[56] References Cited

FOREIGN PATENT DOCUMENTS 0 359 909  3/1990  European Pat. Off. .
1 604 929  5/1971  France .

OTHER PUBLICATIONS

Chemical Abstracts, 105:208 778, (JP 61 076 490). Apr. 18, 1986.

English Language Derwent Abstract of FR 1 604 929. Sep. 19, 1974.

*Primary Examiner*—Shelley A. Dodson
*Attorney, Agent, or Firm*—Finnegan, Henderson, Farabow, Garrett & Dunner, L.L.P.

[57] ABSTRACT

The use of a thermally irreversible photochromic coloring agent, selected in particular from compounds belonging to the diarylethene family and/or those belonging to the fulgide family, as a coloring agent in a cosmetic composition, and to cosmetic compositions comprising it.

24 Claims, No Drawings

USE OF PHOTOCHROMIC COLORING AGENT IN A COSMETIC COMPOSITION, AND COSMETIC COMPOSITION COMPRISING IT

The present invention relates to a novel cosmetic composition, in particular a make-up cosmetic composition or a hair composition, comprising a specific coloring agent which has photochromic properties and which gives novel coloring effects.

Make-up compositions, such as free or compact powders, foundations, blushers, eyeshadows, lipsticks or nail varnishes, consist of a suitable vehicle and of various coloring agents intended to give a certain color to the compositions before and/or after they have been applied to the skin, to mucous membranes, to semi-mucous membranes and/or to the exoskeleton, such as the nails or the hair.

A fairly limited range of coloring agents is nowadays used to create colors, and in particular lakes, inorganic pigments or pearlescent pigments. Lakes give vivid colors but are, for the most part, unstable with respect to light, to temperature or to pH. Some of the lakes also have the drawback of leaving an unsightly stain on the skin after application, by leaching dye. In contrast, the inorganic pigments, in particular the inorganic oxides, are very stable but give colors that are rather dull and pale. In order to obtain colored effects, pearlescent pigments of various colors, but never intense, can also be used, thereby giving iridescent, but usually fairly weak effects.

In the field of the temporary or short-term dyeing of the hair, which gives rise to a slight change in the natural color of the hair, which holds from one shampoo-wash to another and which serves to enhance or correct a shade already obtained, coloring with common pigments has already been proposed in order to give the hair a temporary glint, but the shades obtained by this coloring remain fairly dull, too uniform and lifeless. Such a coloring can in particular be likened to "make-up" for the hair.

It was thus proposed to use photochromic compounds in make-up or hair compositions, so as to obtain pleasant and variable changes in the "color yield" of the make-up effects on the skin and/or the hair.

Photochromic compounds are compounds which have the property of changing color when they are irradiated with a light source, and then regaining their initial color, or a similar color, when the irradiation stops. Such compounds find a particularly advantageous application especially in cosmetic compositions, in particular in make-up compositions such as foundations, blushers or eyeshadows, since it has been observed that the "make-up yield" of a made-up skin differs depending on whether one is under natural light or artificial light. Thus, a make-up effect created under artificial light will appear paler under natural light. In contrast, a make-up effect created in an outdoor environment will appear darker in an artificially lit location.

To overcome this problem, cosmetic compositions have been proposed, for example by European patent EP 359,909, which comprise specific inorganic photochromic compounds selected from metal oxides, their hydrates and their complexes. In particular, that document mentions the use of titanium oxide treated so as to make it photochromic, in make-up compositions such as powders and foundations.

It has also been proposed to use organic photochromic compounds, such as compounds of the spiropyran or naphthoxazine family.

These photochromic compounds are particularly advantageous since they allow a rapid change to be obtained in the coloring of the support onto which they are applied, when the support is exposed to UV, for example, with rapid return to the initial color when the exposure to UV ceases.

Mention may thus be made of patent FR 1,604,929, which describes cosmetic compositions, in particular hair compositions, in the form of an aerosol containing phototropic compounds such as nitrobenzylpyridines, thiosemicarbazones or spiropyran derivatives. After spraying these compositions on the hair and exposure to sunlight, a violet-blue coloring is obtained which returns to pale yellow in the dark.

However, compositions comprising these compounds have the possibility of constantly changing color as a function of the light intensity.

Hence, there is still a need for coloring agents which give, on the one hand, a coloring which changes little or not at all, whether the wearer is in the presence or absence of UV, as is the case with common pigments, while at the same time retaining the possibility of changing color, as the user desires, after illumination under a specific light radiation.

The aim of the present invention is thus to propose a cosmetic composition which comprises such coloring agents and which is thus capable of changing color rapidly, as a function of nature and/or intensity of a specific light radiation, but as the user desires, while at the same time having good cosmetic properties.

The subject of the invention is thus a cosmetic composition comprising, in a cosmetically acceptable medium, at least one thermally irreversible photochromic coloring agent, the coloring agent preferably being selected from compounds belonging to the diarylethene family and/or those belonging to the fulgide family.

Another subject of the invention is the use of a photochromic coloring agent as defined above as a coloring agent in a cosmetic composition.

Another subject of the invention is a process for temporarily coloring and/or making up a support selected from mucous membranes, semi-mucous membranes, the skin and/or the exoskeleton, in which a cosmetic composition as defined above is applied to the support.

Hereinbelow in the present description, the expression "thermally irreversible photochromic coloring agent" is intended to refer to a compound which has thermally irreversible photochromic properties.

The test for determining if a photochromic compound is thermally reversible or irreversible is as follows: the test compound is subjected to an irradiation with UV radiation for a few minutes, preferably for 1 minute, and its color is then determined using a Minolta CM 2002 calorimeter; the values are expressed in terms of H, V and C in the Munsell notation (according to ASTM standard D 1535-68).

Thus, H denotes the shade or Hue, V denotes the intensity or Value and C denotes the purity or Chromaticity.

A value A is thus obtained, which corresponds to the maximum color which can be obtained.

The compound is then left in total darkness for 30 minutes at 25° C. and its color is then redetermined according to the above method; a value B is thus obtained.

When the value B is at least equal to 50% of the value A, it is considered that the compound is thermally irreversible.

Thermally reversible photochromic compounds, such as doped titanium oxide, spiropyrans, spirooxazines or chromenes, are in particular excluded from the context of the present invention.

Without being bound by this explanation, the difference in behavior between the photochromic coloring agents according to the invention and the photochromic compounds according to the prior art may be illustrated in the following way.

When a cosmetic composition according to the invention is applied to a support, a film which is colorless or very faintly colored can be obtained, depending on the choice of the photochromic coloring agent. This film remains colorless or faintly colored irrespective of the light intensity of the environment; when the user so desires, he or she can modify the color of the film, e.g., can obtain a red-colored film, by subjecting the support to a specific UV radiation, of given wavelength. The film turns red and remains so for as long as desired; it is then possible to change the color of the film again, making it once again become colorless or faintly colored, by illumination with radiation of a given wavelength.

It is clear that the colors which can be given to the film depend on the nature of the coloring agents; similarly, the wavelengths required to change these colors are specific to each coloring agent.

In contrast, a composition comprising a photochromic compound according to the prior art, for example a spiropyran or a doped titanium oxide, will give, after application, a colorless or faintly colored film; when the support is exposed to sunlight, the film turns red, for example, and returns to being colorless or faintly colored automatically and very rapidly when the support is in the shade or in an unlit or weakly lit location.

This phenomenon of "decoloring" in the shade is controlled by the use of a photochromic coloring agent according to the invention.

The cosmetic composition according to the invention finds a particularly advantageous application especially in the field of making up the skin, semi-mucous membranes, mucous membranes and/or the exoskeleton.

The term mucous membrane is understood to refer in particular to the inner part of the lower eyelid; the term semi-mucous membranes is intended to refer more particularly to the lips of the face. The term exoskeleton is intended to refer to pilous systems consisting in particular of human head hair, body hairs, the eyelashes and the eyebrows, as well as nails of natural or artificial origin.

The compounds used in the context of the present invention in particular have the advantage of being soluble in the organic solvents usually used in cosmetics, such as alcohols and/or esters.

The composition according to the invention can be in any cosmetically acceptable pharmaceutical form, such as in the form of a lotion, suspension, dispersion or solution in aqueous-alcoholic or solvent medium, which may be multiphasic; in the form of a gel, a mousse, a spray, an oil-in-water, water-in-oil or multiple emulsion; in the form of a free, compact or cast powder; in the form of an anhydrous solid or paste.

The person skilled in the art can select the appropriate pharmaceutical form, as well as the method for preparing it, on the basis of his or her general knowledge, taking into account, on the one hand, the nature of the constituents used, in particular their solubility in the support, and, on the other hand, the application envisaged for the composition.

Among the photochromic coloring agents which can be used in the context of the present invention, the ones preferably selected are those of organic nature, and in particular those belonging to the diarylethene family and/or those belonging to the fulgide family.

The diarylethenes can be represented by formula (I) below:

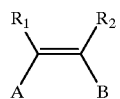

in which the radicals $R_1$ and $R_2$ are always in a "cis" relationship relative to the double bond.

These radicals $R_1$ and $R_2$ can, independently of each other, be selected from optionally fluorinated or perfluorinated $C_1$–$C_{16}$ alkyl radicals, and nitrile radicals.

Mention may be made in particular of the compounds of the following formula:

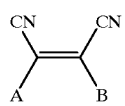

These radicals can also form an optionally fluorinated or perfluorinated ring containing 5 or 6 carbon atoms, in particular according to the following formula:

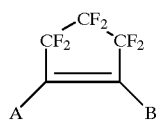

or they can form an anhydride ring containing 5 carbon atoms, and in particular according to the following formula:

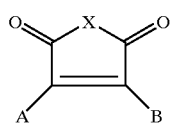

in which X can be an oxygen atom or a radical —N($R_3$)—, with R representing a $C_2$–$C_{16}$ alkyl and/or hydroxyalkyl radical.

The radicals A and B independently represent, in particular, a ring containing 5 atoms or a bicycle containing 5 and 6 atoms, according to the following structures:

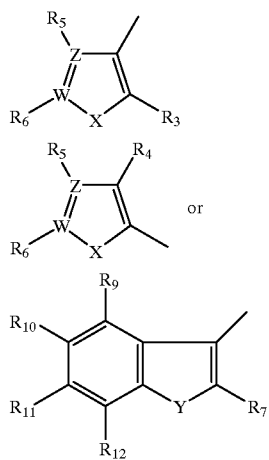

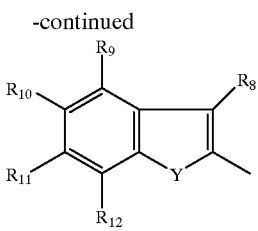

in which

X and Y independently represent an oxygen or sulphur atom or an oxidized form of sulphur, of nitrogen or of selenium, Z and W independently represent a carbon or nitrogen atom, the radicals $R_3$ to $R_{12}$ independently represent hydrogen, a linear or branched $C_1$–$C_{16}$ alkyl or alkoxy group, a halogen, a linear or branched $C_1$–$C_4$ fluoro or perfluoro group, a carboxylic group, a $C_1$–$C_{16}$ alkylcarboxylic group, a $C_1$–$C_{16}$ mono- or dialkylamino group, a nitrile group; a phenyl or naphthalene group or a heterocycle (pyridine, quinoline, thiophene) can be substituted onto these radicals.

However, the groups A and B must not both be equal to an indole structure as shown below:

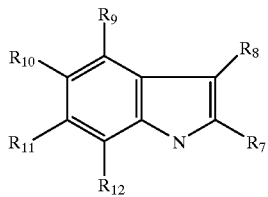

The groups A and B can be separated from the ring by one or two double bonds.

There must always be a group other than hydrogen, for example $CH_3$, CN or $CO_2Et$, on the positions ortho to the junction, between the double bond and the residues A and B, i.e., the groups $R_3$ or $R_5$, $R_4$, $R_7$ and $R_8$ must be other than hydrogen.

It has been observed that the compounds belonging to the diarylethene family have advantageous properties, and in particular they can be converted quantitatively in $10^{-12}$ seconds and that their cyclized form is thermally stable at 80° C. for more than three months.

By way of example, mention may be made of the following compound which can change from colorless to red in the following way, after irradiation at 404–436 nm (return at 546–578 nm):

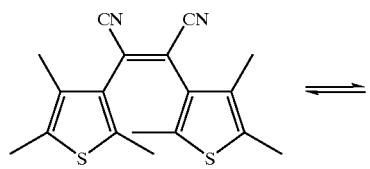

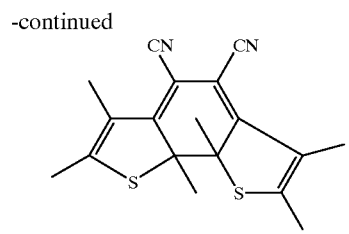

The fulgides can be represented by the following formula:

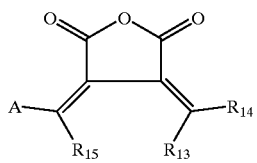

in which the group A has the same meaning as above, the groups $R_{13}$ to $R_{15}$ independently represent a linear or branched $C_1$–$C_{16}$ alkyl group, or alternatively the groups $R_{13}$ and $R_{14}$ can form a ring of 3 to 12 carbon atoms, such as a cyclopropane or an adamantylene.

The photochromic coloring agent can be present in the composition at a content of preferably 0.05–30% by weight, more preferably 0.1–10% by weight. A person skilled in the art can determine the optimum content of photochromic coloring agent, so as to obtain, on the one hand, a cosmetically acceptable composition, and, on the other hand, the desired coloring effect.

The composition according to the invention also contains a cosmetically acceptable medium, i.e., a medium which is compatible with any keratin substance, such as the skin, the nails, the hair, the eyelashes and the eyebrows, mucous membranes and semi-mucous membranes, and any other area of body and facial skin.

The medium can comprise or be in the form of, in particular, a suspension, a dispersion or a solution in aqueous-alcoholic or solvent medium, which may be thickened or even gelled; an oil-in-water, water-in-oil or multiple emulsion; a gel or a mousse; an emulsified gel; a spray; a free, compact or cast powder; an anhydrous paste.

Thus, the composition according to the invention can comprise a fatty phase comprising, in particular, fatty substances which are liquid at 25° C., such as oils of animal, plant, mineral or synthetic origin; fatty substances which are solid at 25° C., such as waxes of animal, plant, mineral or synthetic origin; pasty fatty substances; gums; or mixtures thereof.

The compositions according to the invention can thus comprise volatile oils, which evaporate on contact with the skin, but whose presence in the cosmetic composition is useful since they make the composition easier to spread when it is applied to the skin. Such spreading agents, referred to herein as "volatile oils", are generally oils having, at 25° C., a saturating vapor pressure at least equal to 0.5 millibar (i.e., 50 Pa). Preferably, oils whose flash point is high enough to allow them to be used in formulation, and low enough to give the desired evanescent effect, are used. Oils whose flash point is about 40–100° C. are preferably used. Mention may thus be made of volatile silicone oils such as:

cyclic volatile silicones containing from 3 to 8 and preferably from 4 to 6 silicon atoms. These are, for example, cyclotetradimethylsiloxane, cyclopentadimethylsiloxane or cyclohexadimethylsiloxane, cyclocopolymers of the dimethylsiloxane/methylalkylsiloxane type, such as SILICONE FZ 3109 sold by the company Union Carbide, which is a dimethylsiloxane/methyloctylsiloxane cyclocopolymer, linear volatile silicones containing from 2 to 9 silicon atoms. These are, for example, hexamethyidisiloxane, hexylheptamethyltrisiloxane or octylheptamethyltrisiloxane.

Mention may also be made of volatile hydrocarbon-based oils, such as isoparaffins and in particular isododecane; and fluoro oils, such as the one sold under the name GALDEN (Montefluos).

Non-volatile oils can also be used, among which mention may be made of:

poly($C_1$–$C_{20}$)alkylsiloxanes and in particular those containing trimethylsilyl end groups, preferably those whose viscosity is less than 0.06 m²/s, among which mention may be made of linear polydimethylsiloxanes and alkylmethylpolysiloxanes such as cetyldimethicone (CTFA name), silicones modified with aliphatic and/or aromatic groups, which may be fluorinated, or with functional groups such as hydroxyl, thiol and/or amine groups, phenylsilicone oils, in particular those of formula:

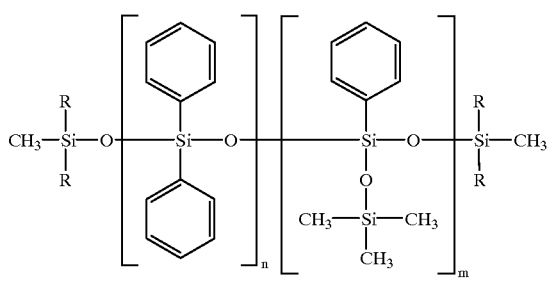

in which R is a $C_1$–$C_{30}$ alkyl radical, an aryl radical or an aralkyl radical, n is an integer ranging from 0 to 100 and m is an integer ranging from 0 to 100, with the proviso that the sum of n+m ranges from 1 to 100, oils of animal, plant or mineral origin, and in particular animal or plant oils formed from fatty acid esters of polyols, in particular liquid triglycerides, for example sunflower oil, corn oil, soybean oil, marrow oil, grapeseed oil, sesame oil, hazelnut oil, apricot oil, almond oil or avocado oil; fish oils, glyceryl tricaprocaprylate, or plant or animal oils of formula $R_1COOR_2$ in which $R_1$ represents a higher fatty acid residue containing from 7 to 19 carbon atoms and $R_2$ represents a branched hydrocarbon-based chain containing from 3 to 20 carbon atoms, for example purcellin oil; liquid paraffin, liquid petroleum jelly, perhydrosqualene, wheatgerm oil, beauty-leaf oil, sesame oil, macadamia oil, grapeseed oil, rapeseed oil, coconut oil, groundnut oil, palm oil, castor oil, jojoba oil, olive oil or cereal germ oil; fatty acid esters; alcohols; acetylglycerides; octanoates, decanoates or ricinoleates of alcohols or of polyalcohols; fatty acid triglycerides; glycerides;

fluoro oils and perfluoro oils.

The composition according to the invention can also comprise other fatty substances, which can be selected by a person skilled in the art based on his or her general knowledge, so as to give the final composition the desired properties, for example in terms of consistency and/or texture. These additional fatty substances can be waxes, gums and/or pasty fatty substances of animal, plant, mineral or synthetic origin, as well as mixtures thereof.

Mention may be made in particular of:

silicone gums, waxes of animal, plant, mineral or synthetic origin, such as microcrystalline waxes, paraffin, petrolatum, petroleum jelly, ozokerite, montan wax; beeswax, lanolin and its derivatives; candelilla wax, ouricurry wax, carnauba wax, Japan wax, cocoa butter, cork fibre wax or sugar cane wax; hydrogenated oils that are solid at 25° C., ozokerites, fatty esters and glycerides that are solid at 25° C.; polyethylene waxes and the waxes obtained by Fischer-Tropsch synthesis; hydrogenated oils that are solid at 25° C.; lanolins; fatty esters that are solid at 25° C.; silicone waxes; fluoro waxes.

The composition according to the invention can also comprise one or more cosmetically acceptable (acceptable tolerance, toxicology and feel) organic solvents. These organic solvents can represent from 0% to 98% of the total weight of the composition. They can be selected from hydrophilic organic solvents, lipophilic organic solvents and amphiphilic solvents, or mixtures thereof.

Among the hydrophilic organic solvents, mention may be made, for example, of linear or branched lower monoalcohols containing from 1 to 8 carbon atoms, such as ethanol, propanol, butanol, isopropanol, isobutanol; polyethylene glycols containing from 6 to 80 ethylene oxides; polyols such as propylene glycol, isoprene glycol, butylene glycol, glycerol, sorbitol; mono- or dialkyl isosorbides in which the alkyl groups contain from 1 to 5 carbon atoms; glycol ethers such as diethylene glycol monomethyl or monoethyl ether and propylene glycol ethers such as dipropylene glycol methyl ether.

As amphiphilic organic solvents, mention may be made of polyols such as polypropylene glycol (PPG) derivatives, such as fatty acid esters of polypropylene glycol, derivatives of PPG and fatty alcohol, such as PPG-23 oleyl ether and PPG-36 oleate.

As lipophilic organic solvents, mention may be made, for example, of fatty esters such as diisopropyl adipate, dioctyl adipate, alkyl benzoates, isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, bis(2-ethylhexyl) succinate, diisostearyl malate, 2-octyldodecyl lactate, glyceryl triisostearate and diglyceryl triisostearate.

The composition according to the invention can also comprise an aqueous phase, which can comprise water, a floral water such as cornflower water and/or a mineral water such as VITTEL, LUCAS or LA ROCHE POSAY.

The aqueous phase can comprise preferably from 0% to 14% by weight, relative to the total weight of the aqueous phase, of a $C_2$–$C_6$ lower monoalcohol and/or of a polyol such as glycerol, butylene glycol, isoprene glycol, propylene glycol or polyethylene glycol.

When the composition according to the invention is in the form of an emulsion, it can also comprise a surfactant, preferably in an amount of from 0.01 to 30% by weight relative to the total weight of the composition.

Among the anionic surfactants which can be used, alone or as a mixture, mention may be made in particular of the alkali metal salts, the ammonium salts, the amine salts or the amino alcohol salts of the following compounds: alkyl sulphates, alkyl ether sulphates, alkylamide sulphates and ether sulphates, alkylarylpolyether sulphates, monoglyceride sulphates, alkyl sulphonates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl sulphoacetates, alkylpropylglycerol carboxylates, alkyl phosphates/alkyl ether phosphates, acyl sarcosinates, alkyl polypeptidates, alkylamido polypeptidates, acyl isethionates and alkyl laurates.

The alkyl or acyl radical in all of these compounds generally denotes a chain of 12 to 18 carbon atoms.

Mention may also be made of soaps and fatty acid salts, such as oleic acid, ricinoleic acid, palmitic acid, stearic acid, coconut oil acid or hydrogenated coconut oil acid, and in particular amine salts such as amine stearates; acyl lactylates in which the acyl radical comprises 8–20 carbon atoms; carboxylic acids of polyglycol ethers corresponding to the formula:

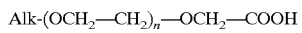

Alk-(OCH$_2$—CH$_2$)$_n$—OCH$_2$—COOH in acid or salified form in which the substituent Alk corresponds to a linear chain containing from 12 to 18 carbon atoms and in which n is an integer ranging from 5 to 15.

Among the nonionic surfactants which can be used, alone or as a mixture, mention may be made in particular of: polyethoxylated, polypropoxylated or polyglycerolated fatty acids, alkylphenols and alcohols with a fatty chain containing 8 to 18 carbon atoms; copolymers of ethylene oxide and of propylene oxide, condensates of ethylene oxide and of propylene oxide on fatty alcohols, polyethoxylated fatty amides, polyethoxylated fatty amines, ethanolamides, fatty acid esters of glycol, oxyethylenated or non-oxyethylenated fatty acid esters of sorbitan, fatty acid esters of sucrose, fatty acid esters of polyethylene glycol, phosphorictriesters, fatty acid esters of glucose derivatives; alkylpolyglycosides and alkylamides of amino sugars; products of condensation of an α-diol, of a monoalcohol, of an alkylphenol, of an amide or of a diglycolamide with glycidol or a glycidol precursor.

The composition according to the invention can also comprise 0 to 5% by weight, relative to the total weight of the emulsion, of at least one co-emulsifier which can be selected from oxyethylenated sorbitan monostearate, fatty alcohols such as stearyl alcohol or cetyl alcohol, or fatty acid esters of polyols, such as glyceryl stearate.

The composition according to the invention can also comprise one or more thickeners in preferred concentrations ranging from 0 to 6% by weight, relative to the total weight of the emulsion. The thickener can be selected from:

polysaccharide biopolymers, such as xanthan gum, carob gum, guar gum, alginates, modified celluloses such as hydroxyethylcellulose, methylcellulose, hydroxypropylcellulose or carboxymethylcellulose, starch derivatives, cellulose ether derivatives containing quaternary ammonium groups, cationic polysaccharides;

synthetic polymers, for instance polyacrylic acids such as polyglyceryl (meth)acrylate polymers, such as HISPAGEL or LUBRAGEL from the companies Hispano Quimica or Guardian, polyvinylpyrrolidone, polyvinyl alcohol, crosslinked polymers of acrylamide and of ammonium acrylate, such as PAS 5161 or BOZEPOL C from Hoechst; acrylate/octylacrylamide copolymers, such as DERMACRYL from National Starch; polyacrylamide-based polymers such as SEPIGEL 305 from SEPPIC, crosslinked polymers of acrylamide and of methacryloyloxyethyltrimethylammonium chloride, such as SALCARE SC 92 from Allied Colloids;

magnesium aluminium silicate.

The thickener can be present in the fatty phase and/or in the aqueous phase.

Depending on the intended application, the composition can also comprise a film-forming polymer. This is especially the case when it is desired to prepare a composition such as a nail varnish, mascara, eyeliner or a hair composition such as a lacquer.

The polymers can be dissolved or dispersed in the cosmetically acceptable medium. In particular, the polymer can be present in the form of a solution in an organic solvent or in the form of an aqueous dispersion of film-forming polymer particles.

The polymer can be selected from nitrocellulose, cellulose acetobutyrate, polyvinyl butyrals, alkyd resins, polyesters, acrylics, vinyls and/or polyurethanes.

Mention may be made in particular of copolymers of (meth)acrylic acid and at least one linear, branched or cyclic (meth)acrylic acid ester monomer and/or at least one linear, branched or cyclic mono- or disubstituted (meth)acrylic acid amide monomer; (meth)acrylic acid/tert-butyl (meth) acrylate copolymers and/or isobutyl (meth)acrylate/C$_1$–C$_4$ alkyl (meth)acrylate copolymers; (meth)acrylic acid/ethyl acrylate/methyl methacrylate terpolymers and tetrapolymers; methyl methacrylate/butyl or ethyl acrylate/ hydroxyethyl or 2-hydroxypropyl acrylate or methacrylate/ (meth)acrylic acid tetrapolymers; copolymers of acrylic acid and of C$_1$–C$_4$ alkyl methacrylate; terpolymers of vinylpyrrolidone, of acrylic acid and of C$_1$–C$_{20}$ alkyl methacrylate, amphoteric polymers; vinyl esters of branched acids; vinyl esters of benzoic acid; copolymers of (meth) acrylic acid and of at least one olefinic monomer; copolymers of vinylic monoacid and/or of allylic monoacid.

Among the resins, mention may be made of resins of arylsulphonamide/formaldehyde or arylsulphonamide/ epoxy type; resins of acrylic, styrene, acrylate/styrene and vinyl type.

The composition can also comprise at least one plasticizer, such as tricresyl phosphate, benzyl benzoate, triethyl citrate, tributyl citrate, triethyl acetyl citrate, tris(2-ethyl)hexyl acetyl citrate, camphor; glycol ethers; castor oil oxyethylenated with 40 mol of ethylene oxide; propylene glycol; butyl glycol; ethylene glycol monomethyl ether acetate; propylene glycol ethers; ester ethers of propylene glycol and of ethylene glycol; diacid esters such as diethyl, dibutyl and diisopropyl phthalates and adipates, diethyl and dibutyl tartrates, diethyl and dibutyl succinates, diethyl and dibutyl sebacates, diethyl, dibutyl and bis(2-ethyl)hexyl phosphates, diethyl or dibutyl acetyl citrate; glycerol esters. Plasticizers can generally be present at a content ranging from 1% to 40% by weight relative to the total weight of the composition.

When the compositions are in the form of an anhydrous nail varnish, the solvent system can preferably represent from about 55% to about 90% by weight relative to the total weight of the varnish. This solvent system can comprise a mixture of various volatile organic solvents, such as ketones, in particular acetone, methyl ethyl ketone or methyl isobutyl ketone; acetates, in particular ethyl acetate, butyl acetate, 2-methoxyethyl acetate, methyl acetate, amyl acetate and isopropyl acetate. The solvent system can also comprise a diluent such as hexane or octane or alternatively an aromatic hydrocarbon such as toluene or xylene, in a proportion in particular of from 10 to 35% by weight relative to the total weight of the varnish.

The composition can also comprise a particulate phase, which can comprise pigments and/or pearlescent agents and/or fillers usually used in cosmetic compositions.

The term pigments should be understood to mean white or colored, inorganic or organic particles intended to color and/or opacify the composition. The term fillers should be understood to mean colorless or white, inorganic or synthetic, lamellar or non-lamellar particles intended to give body or rigidity to the composition, and/or softness, a matte effect and uniformity to the make-up.

The term pearlescent agents should be understood to mean iridescent particles which reflect light.

The pigments can be present in the composition in a proportion preferably ranging from 0 to 15% by weight of the final composition, and more preferably in a proportion of from 8 to 10% by weight. They can be white or colored, inorganic and/or organic, and of common or nanometric size. They can be in the form of a powder or of a pigmentary paste.

Mention may be made of titanium dioxide, zirconium dioxide or cerium dioxide, as well as zinc oxide, iron oxide or chromium oxide, ferric blue, chromium hydrate, carbon black, ultramarine (aluminosilicate polysulphides), manganese pyrophosphate and certain metal powders such as those of silver or of aluminium, and carbon black. Mention may also be made of the lakes commonly used to give a make-up effect to the lips and to the skin, which are calcium, barium, aluminium or zirconium salts, acidic dyes such as halo acid dyes, azo dyes, anthraquinone dyes, etc.

The pearlescent agents can be present in the composition in a proportion preferably from 0 to 20% by weight, more preferably in a proportion from about 8 to about 15% by weight. Among the pearlescent agents which may be envisaged, mention may be made of natural mother-of-pearl, mica coated with titanium oxide, with iron oxide, with natural pigment or with bismuth oxychloride, and colored titanium mica.

The fillers, which can be present preferably in a proportion of from 0 to 30% by weight, more preferably 5 to 15%, in the composition, can be inorganic or synthetic, and lamellar or non-lamellar. Mention may be made of talc, mica, silica, kaolin, Nylon powder, polyethylene powder, Teflon, starch, boron nitride, polymer microspheres such as EXPANCEL (Nobel Industrie), POLYTRAP (Dow Corning) and silicone resin microbeads (TOSPEARLS from Toshiba, for example), precipitated calcium carbonate, magnesium carbonate or hydrocarbonate, and metal soaps derived from organic carboxylic acids containing from 8 to 22 carbon atoms.

Depending on the type of formulation, the pulverulent phase can represent preferably from 0.01 to 99% by weight of the composition.

The composition can also comprise a dye, in particular a natural organic dye such as cochineal carmine, and/or a synthetic dye such as halo acid, azo or anthraquinone dyes. Mention may also be made of inorganic dyes such as copper sulphate.

The composition can also comprise any additive usually used in the cosmetic field, such as antioxidants, fragrances, essential oils, preserving agents, lipophilic or hydrophilic cosmetic active agents, moisturizers, vitamins, dyes, essential fatty acids, sphingolipids, self-tanning agents such as DHA, sunscreens, antifoaming agents, sequestering agents and antioxidants.

Needless to say, a person skilled in the art will take care to select the optional complementary compounds, and/or the amount thereof, such that the advantageous properties of the composition according to the invention are not, or are not substantially, adversely affected by the addition envisaged.

The cosmetic compositions according to the invention include those concerning facial make-up, i.e., eyeshadows, eyeliners, mascaras, powders, foundations, blushers, tinted creams, lip compositions, lip pencils or concealer sticks, as well as make-up for the hair, in particular gels, creams or mousses for temporarily coloring the hair, and make-up for the nails, in particular anhydrous nail varnishes.

The anhydrous compositions can be present in the form of free or compacted powder, solid, pasty or liquid make-up possibly containing a binder which can preferably represent from 0.01 to 95% by weight relative to the total weight of the composition. The hair compositions according to the invention can be in the form of compositions pressurized as an aerosol in the presence of a propellant. The compositions according to the invention can also be in the form of a gel or an aqueous or aqueous-alcoholic solution of one or more water-soluble polymers such as polyacrylic acid derivatives, or in the form of emulsified gels obtained by dispersion of oils in gels using emulsifiers, such as the Pemulens from the company Goodrich. The compositions according to the invention can also be in the form of a stick and can contain fillers and a binder which can preferably represent from 0.01 to 95% by weight relative to the total weight of the composition.

The invention is illustrated in greater detail in, but is not limited by, the examples which follow.

EXAMPLE 1

A face cream was prepared in the form of an oil-in-water emulsion having the following composition (% by weight):

| A face cream was prepared in the form of an oil-in-water emulsion having the following compostion (% by weight): | |
|---|---|
| oils (mineral, silicone and hydrocarbon-based) | 20% |
| gel containing 5% magnesium aluminium silicate | 20% |
| cellulose gum | 3.5% |
| surfactant | 4% |
| preserving agents | q.s |
| water | qs 100% |
| coloring agent according to the invention 2,3-bis(2,4,5-trimethyl-3-thiophenyl)-2-butene-dinitrile | 2% |

When the composition according to the invention was applied to the back of the hand, and after irradiation, a healthy appearance was obtained.

EXAMPLE 2

A hair lotion was prepared, having the following composition:

| A hair lotion was prepared, having the following composition: | |
|---|---|
| film-forming polymer at 30% in a 50/50 aqueous-alcoholic solution | 9% |
| ethanol | 35% |
| water | qs 100% |
| coloring agent according to the invention 2,3-bis(2,4,5-trimethyl-3-thiophenyl)-2-butene-dinitrile | 5% |

When applied to chestnut-colored hair, without rinsing out, this lotion gave the hair glints, after drying and irradiation.

EXAMPLE 3

An anhydrous nail varnish was prepared, having the following composition:

| An anhydrous nail varnish was prepared, having the following composition: | |
| --- | --- |
| nitrocellulose | 15% |
| toluenesulphonamide/formaldehyde resin | 10% |
| tributyl acetyl citrate | 6% |
| butyl acetate | 20% |
| ethyl acetate | 10% |
| toluene | qs 100% |
| coloring agent according to the invention 2,3-bis(2,4,5-trimethyl-3-thiophenyl)-2-butene-dinitrile | 4% |

The varnish obtained was colorless to pale yellow in the bottle. On applying this nail varnish directly onto the nails, and after irradiation, a pale pink effect was obtained.

This varnish can also be applied to false nails.

Precut templates to be applied to the nails before illumination can also be used, so as to be able to draw patterns or write on the nails.

Different coloring agents for each nail can also be used, so as to obtain nails of different colors.

EXAMPLE 4

An aqueous nail varnish was prepared, having the following composition:

| An aqueous nail varnish was prepared, having the following composition: | |
| --- | --- |
| aqueous dispersion of polyester-polyurethane (35.8% solids) | 55% |
| aqueous dispersion of acrylic polymer (solids; 45.5%) | 18% |
| associative polyurethane thickener | 0.8% |
| water | qs 100% |
| coloring agent according to the invention 2,3-bis(2,4,5-trimethyl-3-thiophenyl)-2-butene-dinitrile | 3% |

This varnish can also be applied to false nails.

EXAMPLE 5

Nail varnish compositions were prepared, comprising the following ingredients:

| Nail varnish compositions were prepared, comprising the following ingredients: | |
| --- | --- |
| nitrocellulose | 15% |
| toluenesulphonamide/formaldehyde resin | 10% |
| tributyl acetyl citrate | 6% |
| butyl acetate | 20% |
| ethyl acetate | 10% |
| 2,3-bis(2,4,5-trimethyl-3-thiophenyl)-2-butenedinitrile | x %* |
| toluene | qs 100% |

*the values for x are shown in the tables below

The compositions obtained were pale-yellow to yellow in the bottle stored away from the light, and red if the bottle was exposed to daylight.

On applying these yellow compositions to nails, and after irradiating with a light source at a wavelength of about 400 nm, a pink to red effect was obtained.

These compositions can also be applied to false nails.

The compositions prepared above are applied to false nails and irradiated using the following two lamps:

Philips SOX-E18 lamp, of wavelength 596 nm

UV lamp with filter, for thin layer chromatography, of wavelength 365 nm

Their color was then measured using a Minolta CM 2002 colorimeter; the values are expressed in terms of H, V, C in the Munsell notation (according to ASTM standard D 1535-68).

The following results were obtained:

TABLE 1

| after irradiation at 596 nm | | | | | | |
| --- | --- | --- | --- | --- | --- | --- |
| x(%) | H | V | C | L | a | b |
| 0 | 4.73 | 8.0 | 3.0 | 80.40 | −2.01 | 20.77 |
| 0.125 | 6.73 | 7.4 | 3.2 | 75.56 | −4.09 | 23.03 |
| 0.25 | 7.77 | 7.3 | 3.6 | 73.94 | −5.67 | 26.08 |
| 0.5 | 6.87 | 7.2 | 5.0 | 72.88 | −5.88 | 35.55 |
| 1.125 | 6.27 | 6.7 | 5.9 | 67.82 | −5.03 | 42.07 |
| 2.5 | 6.67 | 7.9 | 8.3 | 79.90 | −7.97 | 59.10 |
| 5 | 6.17 | 7.4 | 8.8 | 74.97 | −6.44 | 62.34 |
| 10 | 6.90 | 7.2 | 8.1 | 72.68 | −7.81 | 57.97 |

TABLE 2

| after irradiation at 365 nm | | | | | | |
| --- | --- | --- | --- | --- | --- | --- |
| x(%) | H | V | C | L | a | b |
| 0 | 4.80 | 7.9 | 2.9 | 80.36 | −2.03 | 20.94 |
| 0.125 | 3.17 | 5.9 | 6.2 | 59.83 | 19.85 | 29.89 |
| 0.25 | 4.77 | 4.7 | 9.4 | 47.32 | 39.68 | 19.76 |
| 0.5 | 8.90 | 4.6 | 8.9 | 47.05 | 35.23 | 29.73 |
| 1.125 | 7.83 | 4.3 | 8.8 | 44.40 | 36.42 | 26.70 |
| 2.5 | 9.67 | 5.0 | 10.4 | 51.34 | 39.78 | 37.93 |
| 5 | 9.43 | 4.8 | 10.4 | 48.49 | 39.85 | 36.86 |
| 10 | 0.00 | 4.7 | 9.5 | 48.11 | 35.76 | 35.56 |

TABLE 3

| after irradiation in daylight | | | | | | |
| --- | --- | --- | --- | --- | --- | --- |
| x(%) | H | V | C | L | a | b |
| 0 | 4.73 | 8.0 | 3.0 | 80.40 | −2.01 | 20.77 |
| 0.125 | 0.23 | 6.8 | 4.6 | 69.35 | 4.07 | 30.28 |
| 0.25 | 2.13 | 5.9 | 5.4 | 60.22 | 18.56 | 24.31 |
| 0.5 | 0.07 | 5.0 | 7.9 | 51.24 | 29.95 | 30.01 |
| 1.125 | 5.40 | 3.9 | 10.0 | 39.32 | 42.83 | 22.31 |
| 2.5 | 5.70 | 4.1 | 12.1 | 42.52 | 51.28 | 29.01 |
| 5 | 4.60 | 3.5 | 11.7 | 36.00 | 50.09 | 23.20 |
| 10 | 4.50 | 3.5 | 11.0 | 35.81 | 47.52 | 21.51 |

I claim:

1. A cosmetic composition comprising, in a cosmetically acceptable medium, at least one thermally irreversible photochromic coloring agent.

2. A cosmetic composition according to claim 1, wherein said at least one thermally irreversible photochromic coloring agent is a diarylethene compound or a fulgide compound.

3. A cosmetic composition according to claim 2, wherein said diarylethene compound corresponds to formula (I):

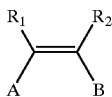

in which:

R$_1$ and R$_2$ are always in a "cis" relationship relative to the double bond, and are independently selected from optionally fluorinated or perfluorinated C$_1$–C$_{16}$ alkyl radicals, nitrite radicals CN; or together form an optionally fluorinated or perfluorinated ring containing 5 or 6 carbon atoms; or together form an anhydride ring containing 5 carbon atoms; and A and B independently represent a ring containing 5 atoms or a bicycle containing 5 atoms in one ring and 6 atoms in a second ring, according to the following structures:

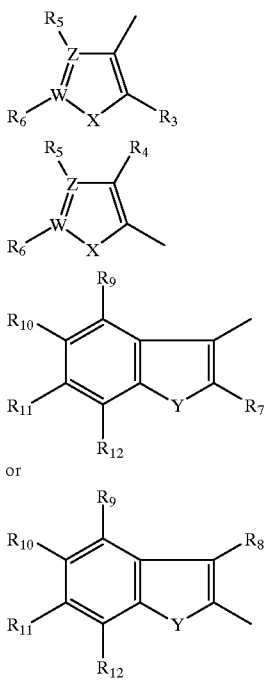

or in which:

X and Y independently represent an oxygen or sulphur atom or an oxidized form of sulphur, nitrogen or selenium, Z and W independently represent a carbon or nitrogen atom, R$_3$ to R$_{12}$ independently represent a hydrogen, a linear or branched C$_1$–C$_{16}$ alkyl or alkoxy group, a halogen, a linear or branched C$_{1-C4}$ fluoro or perfluoro group, a carboxylic group, a C$_1$–C$_{16}$ alkylcarboxylic group, a C$_1$–C$_{16}$ mono- or dialkylamino group, a nitrile group, wherein any of said groups may be optionally substituted by a phenyl or naphthalene group or a heterocycle, wherein A and B may be separated from the ring by one or two double bonds, and further wherein A and B are not both equal to the following indole structure:

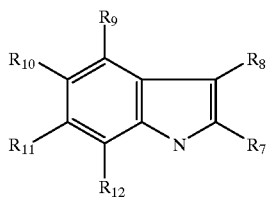

in which at least one group on positions ortho to the junction between the double bond and A and B is not hydrogen.

4. A cosmetic composition according to claim 3, wherein when R$_1$ and R$_2$ form an anhydride ring containing 5 carbon atoms, said ring corresponds to the following formula:

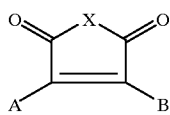

in which:

X is an oxygen atom or a radical —N(R$_3$)—, wherein R$_3$ is a C$_2$–C$_{16}$ alkyl or a hydroxyalkyl radical, and A and B are as defined in claim 3.

5. A cosmetic composition according to claim 3, wherein when one or more of R$_3$ to R$_{12}$ is substituted by a heterocycle, said heterocycle is pyridine, quinoline, or thiophene.

6. A cosmetic composition according to claim 3, wherein said diarylethene compound corresponds to formula:

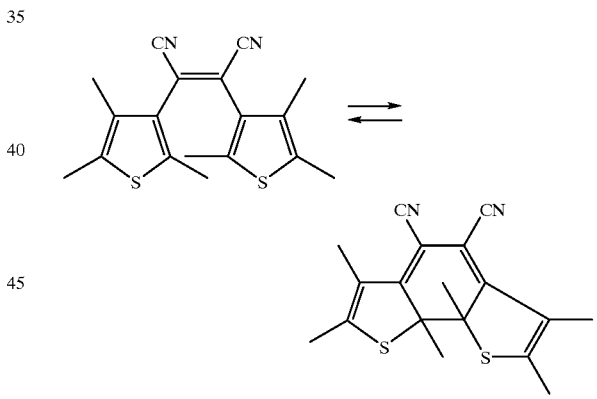

7. A cosmetic composition according to claim 2, wherein said fulgide compound is represented by the following formula:

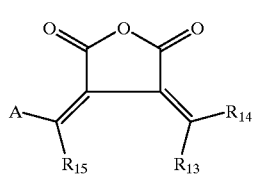

in which

A represents a ring containing 5 atoms or a bicycle containing 5 atoms in one ring and 6 atoms in a second ring, according to the following structures:

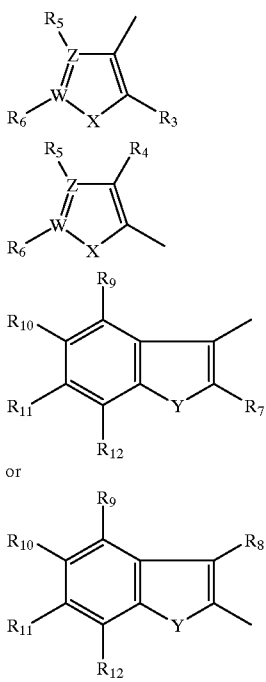

in which:

X and Y independently represent an oxygen or sulphur atom or an oxidized form of sulphur, nitrogen or selenium, Z and W independently represent a carbon or nitrogen atom, $R_3$ to $R_{12}$ independently represent a hydrogen, a linear or branched $C_1$–$C_{16}$ alkyl or alkoxy group, a halogen, a linear or branched $C_1$–$C_4$ fluoro or perfluoro group, a carboxylic group, a $C_1$–$C_{16}$ alkylcarboxylic group, a $C_1$–$C_{16}$ mono- or dialkylamino group, or a nitrile group; wherein any of said groups may be optionally substituted by a phenyl or naphthalene group or a heterocycle, wherein A may be separated from the ring by one or two double bonds; and $R_{13}$ to $R_{15}$ independently represent a linear or branched $C_1$–$C_{16}$ alkyl group, or $R_{13}$ and $R_{14}$ form a ring of 3 to 12 carbon atoms.

8. A cosmetic composition according to claim 6, wherein when $R_{13}$ and $R_{14}$ form a ring of 3 to 12 carbon atoms, said ring is a cyclopropane or an adamantylene.

9. A cosmetic composition according to claim 1, wherein said at least one thermally irreversible photochromic coloring agent is present in an amount ranging from 0.05 to 30% by weight relative to the total weight of said cosmetic composition.

10. A cosmetic composition according to claim 9, wherein said at least one thermally irreversible photochromic coloring agent is present in an amount ranging from 0.1 to 10% by weight relative to the total weight of said cosmetic composition.

11. A cosmetic composition according to claim 1, further comprising a fatty phase comprising at least one fatty substance which is liquid at 25° C.; at least one fatty substance which is solid at 25° C.; at least one pasty fatty substance; a gum; a volatile oil, or a mixture thereof.

12. A cosmetic composition according to claim 11, wherein said at least one fatty substance which is liquid at 25° C. is an oil of animal, plant, mineral or synthetic origin and said at least one fatty substance which is solid at 25° C. is a wax of animal, plant, mineral or synthetic origin.

13. A cosmetic composition according to claim 1, further comprising at least one cosmetically acceptable organic solvent.

14. A cosmetic composition according to claim 13, wherein said at least one cosmetically acceptable organic solvent is present in an amount up to 98% by weight relative to the total weight of said cosmetic composition.

15. A cosmetic composition according to claim 13, wherein said at least one cosmetically acceptable organic solvent is a hydrophilic organic solvent, a lipophilic organic solvent, an amphiphilic solvent, or a mixture thereof.

16. A cosmetic composition according to claim 1, further comprising at least one component selected from an aqueous phase, a surfactant, a thickener, a film-forming polymer, a co-emulsifier, a plasticizer, and a particulate phase.

17. A cosmetic composition according to claim 16, wherein when said cosmetic composition further comprises an aqueous phase, said aqueous phase may comprise up to 14% by weight, relative to the total weight of said aqueous phase, of at least one component selected from a $C_2$–$C_6$ lower monoalcohol and a polyol.

18. A cosmetic composition according to claim 16, wherein said particulate phase comprises pigments, pearlescent agents, fillers, or a mixture thereof.

19. A cosmetic composition according to claim 1, wherein said cosmetic composition is in the form of a lotion, a suspension, a dispersion or a solution in aqueous-alcoholic or solvent medium; an oil-in-water, water-in-oil or multiple emulsion; a gel or a mousse; an emulsified gel; a spray; a free, compact or cast powder; or an anhydrous solid or paste.

20. A cosmetic composition according to claim 1, wherein said cosmetic composition is a make-up composition for the face, body, hair, or nails.

21. A cosmetic composition according to claim 20, wherein said make-up composition for the face is an eyeshadow, eyeliner, mascara, powder, foundation, blusher, tinted cream, lip composition, lip pencil or concealer stick; said make-up composition for the hair is a gel, cream or mousse for temporarily coloring hair; and said make-up composition for the nails is nail varnish.

22. A method of coloring a cosmetic composition comprising including said at least one thermally irreversible photochromic coloring agent in said cosmetic composition as a coloring agent.

23. A process for temporarily coloring and/or making up a support comprising applying at least one cosmetic composition according to claim 1 to said support.

24. A process according to claim 23, wherein said support is skin, exoskeleton, a mucous membrane, or a semi-mucous membrane.

* * * * *

UNITED STATES PATENT AND TRADEMARK OFFICE
CERTIFICATE OF CORRECTION

PATENT NO. : 6,123,952
DATED : September 26, 2000
INVENTOR(S) : Alain LAGRANGE

It is certified that error appears in the above-indentified patent and that said Letters Patent is hereby corrected as shown below:

Claim 3, col. 15, line 12, "nitrite" should read --nitrile--.
line 58, "$C_{1-C4}$" should read --$C_1$-$C_4$--.

Signed and Sealed this

Fifteenth Day of May, 2001

Attest:

NICHOLAS P. GODICI

Attesting Officer     *Acting Director of the United States Patent and Trademark Office*

UNITED STATES PATENT AND TRADEMARK OFFICE
CERTIFICATE OF CORRECTION

PATENT NO.   : 6,123,952
DATED        : September 26, 2000
INVENTOR(S)  : Alain Lagrange It is certified that error appears in the above-identified patent and that said Letters Patent is hereby corrected as shown below:

Column 15,
Line 12, "nitride" should read -- nitrile --.
Line 58, "$C_{1-C4}$" should read -- $C_1$-$C_4$ --.

Signed and Sealed this

Fifth Day of October, 2004

JON W. DUDAS
*Director of the United States Patent and Trademark Office*